United States Patent
Penco et al.

(10) Patent No.: US 6,589,939 B2
(45) Date of Patent: Jul. 8, 2003

(54) CAMPTOTHECIN DERIVATIVES HAVING ANTITUMOR ACTIVITY

(75) Inventors: Sergio Penco, Milan (IT); Lucio Merlini, Milan (IT); Paolo Carminati, Pomezia (IT); Franco Zunino, Milan (IT)

(73) Assignee: Sigma-Tau Industrie Farmaceutiche Riunite S.p.A., Milan (IT)

( * ) Notice: Subject to any disclaimer, the term of this patent is extended or adjusted under 35 U.S.C. 154(b) by 90 days.

(21) Appl. No.: 09/741,818

(22) Filed: Dec. 22, 2000

(65) Prior Publication Data

US 2001/0008939 A1 Jul. 19, 2001

Related U.S. Application Data

(62) Division of application No. 09/507,928, filed on Feb. 22, 2000, now Pat. No. 6,242,457.

(30) Foreign Application Priority Data

Mar. 9, 1999 (EP) ............................................. 99830124

(51) Int. Cl.⁷ ........................ A61K 31/70; A61K 31/44; C07H 15/24; C07D 498/22
(52) U.S. Cl. ............................ 514/25; 514/33; 514/280; 514/283; 536/4.1; 536/17.2; 536/18.7; 546/48
(58) Field of Search ..................... 514/25, 33, 280, 514/283; 546/48; 536/4.1, 18.1, 17.2

(56) References Cited

U.S. PATENT DOCUMENTS

| | | | |
|---|---|---|---|
| 4,399,276 A | * 8/1983 | Miyasaka et al. | 542/416 |
| 5,614,529 A | * 3/1997 | Wall et al. | 514/279 |
| 5,633,016 A | * 5/1997 | Johnson | 424/649 |
| 5,972,955 A | * 10/1999 | Duvvuri et al. | 514/283 |

FOREIGN PATENT DOCUMENTS

| WO | WO 97/31003 | | 8/1997 |
|---|---|---|---|
| WO | WO 98/07727 | * | 2/1998 |

OTHER PUBLICATIONS

Sawada, S. et al "Chemical modification of an antitumor alkaloid camptothecin" 1991, vol. 39, No. 10, pp. 2574–2580.*

Sawada, S. et al "Chemical modification of an antitumor alkaloid camptothecin" Chem. Pharm. Bull., vol. 39, No. 10, pp. 2574–2580.

Barstow, K. et al "Antitumor agents . . . " Bioorg. Med. Chem. vol. 5, No. 8, pp. 1481–1488, 1997.

CAS abstract of WO 98/07727, 1998.

Wang, H.–K. et al "Novel water–soluble 7–acylhydrazono–(–formyl camptothecins . . . " Bioorg. & Med Chem. Lett. vol. 4, No. 4, pp. 579–582, 1994.

* cited by examiner

Primary Examiner—James O. Wilson
Assistant Examiner—Leigh C. Maier
(74) Attorney, Agent, or Firm—Nixon & Vanderhye P.C.

(57) ABSTRACT

Camptothecin derivatives of camptothecin of formula (I):

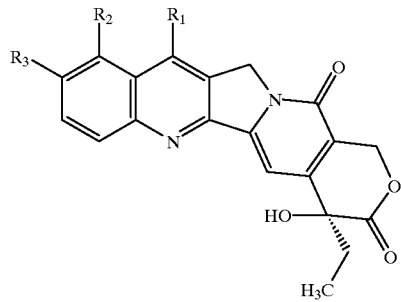

wherein the groups $R_1$, $R_2$ and $R_3$ are as defined in the description are disclosed.

The compounds of formula (I) are endowed with antitumor activity and show a good therapeutic index.

Processes for the preparation of the compounds of formula (I) and their use in the preparation of medicaments useful in the treatment of tumors, viral infections and antiplasmodium falciparum are also disclosed.

4 Claims, No Drawings

CAMPTOTHECIN DERIVATIVES HAVING ANTITUMOR ACTIVITY

This is a division of application Ser. No. 09/507,928, filed Feb. 22, 2000, now U.S. Pat. No. 6,248,457, the entire content of which is hereby incorporated by reference in this application.

The present invention relates to compounds having antitumor activity, in particular to new derivatives of camptothecins, processes for their preparation, their use as antitumor drugs and pharmaceutical compositions containing them as active ingredients.

BACKGROUND OF THE INVENTION

Camptothecin is an alkaloid, which was isolated by Wall et al (J. Am. Chem. Soc. 83, 3888–3890 (1966)) for the first time from the tree Camptoteca acuminata, a plant originating from China, of the Nyssaceae family.

The molecule consists of a pentacyclic structure having a lactone in the ring E, which is essential for cytotoxicity.

The drug demonstrated a wide spectrum of antitumor activity, in particular against colon tumors, other solid tumors and leukemias, and the first clinical trials were performed in the early 70's. Since Camptothecin (in the following briefly CPT) has low water solubility and in order to prepare clinical trials, the National Cancer Institute (NCI) prepared the sodium salt (NSC100880), which is water-soluble. Clinical trials in phase I and II, were not completed because of the high toxicity showed by the compound (hemorrhagic cystitis, gastrointestinal toxicity, such as nausea, vomit, diarrhoea, and myelosuppression, especially leucopenia and thrombocytopenia.

In any case, sodium salt showed a lower activity than CPT, because, at pH 7.4, the inactive form (open ring) predominates on the lactone-active one (closed ring), which predominates at pH<4.0.

Subsequently, many CPT analogues were synthesised in order to obtain compounds with lower toxicity and higher water solubility. Two drugs are marketed, Irinotecan (CPT-11), marketed with the Trade Mark Camptosar® by Upjohn and Topotecar®, marketed with the Trade Mark Hymcamptamin® or Thycantin®, by Smith Kline & Beecham. Other derivatives are in different steps of clinical development in phase II, such as NSC-603071 (9-aminocamptothecin), 9-NC or 9-nitrocamptothecin, an oral prodrug converted in 9-aminocamptothecin, GG-211 (GI 147211), and DX-8591f, the latter being water-soluble. All the derivatives identified to-date contain the parent structure with 5 rings, essential for cytotoxicity. It was demonstrated that modifications on the first ring, such as in the case of the above-mentioned drugs increase water solubility and allow a higher tolerability of the drug.

Water-soluble Irinotecan was approved for the treatment of many solid tumors and ascites (colon-rectum, skin, stomach, breast, small and non-small cell lung, cervix and ovarian cancer and in non-Hodgkin lymphoma). Moreover, Irinotecan resulted active in solid tumors resistant to Topotecan, vincristine or melphalan and MDR-1 cells resulted marginally resistant to the drug. The active metabolite was identified as the 10-hydroxyderivatives (SN-38), produced by the action of carboxylesterases. CPT-11 showed a good activity using different administration routes, such as intraperitoneal, intravenous, oral (Costin D., Potmhexyl M. Advances in Pharmacol. 29B, 51–72 1994).

CPT-11 was administered also with cisplatin or etoposide, showing a synergistic effect, thanks to the ability to hinder DNA repair. Also in this case, however, a grade 3 and 4 leucopenia and diarrhoea arose (Sinha B. K. (1995) Topoisomerase inhibitors. Drugs 49, 11–19, 1995).

Topotecan has a significant oral bioavailability. Oral administration proved to be convenient to reach a prolonged exposition to the drug, without the use of temporary catheters being necessary (Rothenberg M. L. Annals of Oncology 8, 837–855, 1997). Also this water-soluble CPT analogue showed activity against different types of tumors, with different administration routes, intraperitoneal, intravenous, subcutaneous, oral The more promising results were obtained with Topotecan hydrochloride, intravenous infusion for 5 days, in different tumors such as small and non-small cell lung, ovarian, breast, stomach, liver, prostatae, soft tissue sarcoma, head and neck, oesophagus, resistant colon-rectum, multiform glioblastoma, chronic and acute myelocytic leukemias. However, also in this case, severe side effects occurred, such as neutropenia and thrombocytopenia, whereas gastrointestinal toxicity, such as nausea, vomit and diarrhoea were milder.

It was demonstrated that the main transformation and elimination pathways of the drug comprise lactone hydrolysis and urinary excretion: in fact, lactone form is 50% hydrolysed to open ring, 30 min after infusion. Topotecan crosses hematoencephalic barrier 10 min after infusion (30% in the cerebrospinal fluid with respect to plasma). On the contrary, camptothecin does not cross hematoencephalic barrier in significant amount, probably due to its binding with proteins.

Clinical development of 9-aminocamptothecin was hampered by its scarce water solubility. Recently, a colloidal dispersion was prepared, which made possible its entry in phase II clinical trial. Prolonged exposition (from 72 hours to 21 days) appeared to be essential to demonstrate antitumor activity, because of its short half-life (Dahut et al., 1994). Responses in patients suffering from not treated colon-rectum, and breast cancer and resistant lymphoma, were noticed. The activity demonstrated against Pgp-positive tumors suggested a lack of cross-resistance against resistant MDR-1 cells. Once again, bone marrow and gastrointestinal toxicity was observed.

Lurtotecan is the most water-soluble analogue, with an activity comparable to Topotecan in vitro. Two regimens were adopted: one 30-min infusion a day for 5 days every 3 weeks and one 72-hours infusion one time every 3 weeks. Responses in patients suffering from, neck, ovarian, breast, liver tumour were observed. Also in this case, hematic toxicity was detected. The molecule is the following:

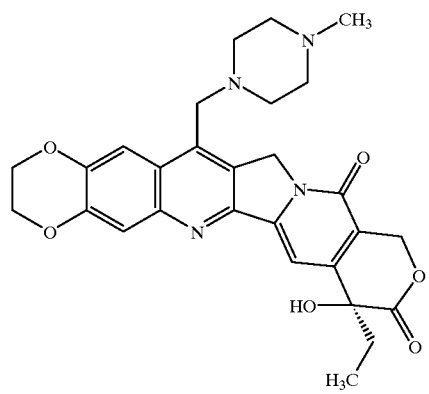

9-Nitrocamptothecin is an oral prodrug rapidly converted into 9-aminocamptothecin after administration. Responses were observed in patients suffering from pancreas, ovarian, and breast cancer.

Notwithstanding the major part of tumour cells is highly sensitive to topoisomerase I inhibitors, due to the high enzyme levels, some tumoral lines result to be resistant. This is due to other mechanisms, rather than the overexpression of MDR1 and MRP (multidrug resistance associated protein) genes and of their products, P (Pgp) glycoprotein and MRP protein, respectively, for which Topotecan or CPT-11 are not very good substrates, (Kawato Yet al J. Pharm. Pharmacol. 45, 444–448, (1993)).

In fact, it was observed that some resistant tumour cells contain mutant forms of topo I, accordingly the formation of the topo I-DNA complex is damaged or some cells lack in the carboxylesterase activity, necessary for converting CPT-11 in the active metabolite SN-38 and are thus resistant against this drug (Rothenberg, 1997, ibid.).

Within the drugs used in tumour therapy, the interest in inhibitors of topoisomerase I enzymes is attributed to the following considerations: a) efficacy against tumors naturally resistant to conventional drugs, topoisomerase II inhibitors included; b) the levels of the toco I enzyme remain elevated in all phases of the cycle; c) many tumors express high levels of the target enzyme; d) lack of recognition by the proteins involved in the phenomenon of multi-drug resistance (Pgp or MRP) and absence of the detoxifying enzyme-mediated metabolism, associated to the glutathione-dependent system (glutathione peroxidase and glutathione S-transferase) (Gerrits C J H., et al., Brit. J. Cancer 76, 952–962).

Once potential clinical advantages of topoisomerase I inhibitors are taken into consideration, both in terms of antitumor activity, assayed on a wide range of tumors, and the poor induction of pharmaco-resistance, the present research aims to identify topo I inhibitors with a lower toxicity with respect to the one demonstrated by the drugs on the market or in clinical phase. The factors determining the relative potency of camptothecin analogues include a) intrinsic activity of topoisomerase I inhibition; b) drug mean life; c) interaction with plasma proteins; d) the ratio between the circulating active form (lactone) and the non active one (carboxylate); e) drug sensitivity relative to cell outflow mediated by glycoprotein P or MRP; f) bond stability with topoisomerase I (Rothenberg, 1997, ibid.).

Among the main adverse effects of Irinotecan and other camptothecins derivatives, myelosuppression and gastrointestinal toxicity, such as diarrhoea and vomit, have been observed. Diarrhoea can have an early or late onset and can be a dose-limiting factor. Vomit and late diarrhoea are induced by many antitumor drugs, while early diarrhoea occurring during or immediately after infusion is almost specific for Irinotecan and some camptothecin derivatives.

Toxic effects occur mainly in the intestinal tract.

In order to reduce diarrhoea, CPT-11 was administered in some clinical trials, in combination with loperamide, a synthetic oppioid, agonist of the mu-oppioid enteric receptors (Abigerges, 1994; Abigerges, 1995), as well as with an inhibitor of the enkephalinases (acetorfan) or with ondansetron, an antagonist of the 5-HT3 receptors, or with diphenidramine, an antagonist of H1 receptors.

To date, the problems connected with the use of camptothecin derivatives as antitumor drugs can be summarised in the following items:

camptothecin (CPT), and many of its active derivatives have low water solubility;

the subsequent derivatives are endowed with severe side effects at gastrointestinal and bone marrow level;

some tumour lines developed resistance against topoisomerase I inhibitors;

there is the constant search for a better therapeutic index.

Patent application WO97/31003, herein incorporated for reference, discloses derivatives of camptothecins substituted at positions 7, 9 and 10. Position 7 provides the following substitutions: —CN, —CH(CN)—$R_4$, —CH=C(CN)—$R_4$, —$CH_2$—CH=C(CN)—$R_4$, —C(=NOH)—$NH_2$, —CH=C($NO_2$)—$R_4$, —CH(CN)—$R_5$, —CH($CH_2NO_2$)—$R_5$, 5-tetrazolyl, 2 -(4,5-dihydroxazolyl), 1,2,4-oxadiazolidin-3-yl-5-one, wherein $R_4$ is hydrogen, linear or branched alkyl from 1 to 6 carbon atoms, nitrile, carboxyalkoxy. Of these possible compounds, WO97/31003 enables the disclosure only of camptothecin derivatives bearing at position 7 the group —CN and —CH=C(CN)$_2$, with unsubstituted positions 9 and 10.

Of these compounds, the best one proved to be the 7-nitrile ($R_4$=—CN), hereinafter named CPT 83, with cytotoxic activity on non-small cells lung carcinoma (non-SCLC, H-460). This tumour line is intrinsically resistant to cytotoxic therapy and is only moderately responsive to topoisomerase I inhibitors, notwithstanding the overexpression of the target enzyme. CPT 83 is more active than Topotecan, taken as reference compound and on the whole it offers a better pharmacological profile, even in terms of tolerability, then a better therapeutic index.

CPT 83 is prepared through a synthesis route comprising the oxidation of 7-hydroxymethylcamptothecin to camptothecin 7-aldehyde, the transformation of the latter into oxime and final conversion into nitrile.

The starting compound and the intermediates are disclosed in Sawada et al Chem. Pharm. Bull. 39, (10) 2574 (1991). This paper makes reference to a patent family with priority of 1981, for example European patent application EP 0056692, published in 1982, incorporated herein for reference. In these publications there are disclosed, among others, the compounds camptothecin 7-aldehyde and its oxime. The usefulness of these derivatives is to provide compounds with antitumor activity having low toxicity starting from 7-hydroxymethylcamptothecin. In the paper published on Chem. Pharm. Bull. 39, (10) 2574 (1991), the authors demonstrate that, with respect to camptothecin, the 7-alkyl and 7-acyloxymethyl derivatives, which were not foreseen in the above mentioned patent application, are the more active compounds on lines of murine leukemia L12 10, while lower activity, always with respect to camptothecin, was observed in compounds bearing 7-substitutions with high polar character, such as hydrazones and the oxime —CH(=NOH).

ABSTRACT OF THE INVENTION

It has now surprisingly been found that camptothecins bearing an alkyloxime O-substituted at position 7 are endowed with antitumor activity higher than the compound of reference Topotecan. More surprisingly, it has been found that camptothecins bearing an enamino group on position 7, are also endowed with antitumor activity. Said compounds have better therapeutic index.

Accordingly, it is an object of the present invention compounds of general formula (I):

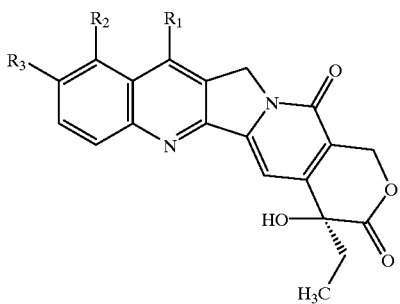

wherein: $R_1$ is a —$C(R_5)$=N—$O_{(n)}R_4$ group, wherein $R_4$ is hydrogen or a $C_1$–$C_8$ linear or branched alkyl or $C_1$–$C_8$ linear or branched alkenyl group or $C_3$–$C_{10}$ cycloalkyl, or ($C_3$–$C_{10}$) cycloalkyl —($C_1$–$C_8$) linear or branched alkyl group, or $C_6$–$C_{14}$ aryl, or ($C_6$–$C_{14}$) aryl —($C_1$–$C_8$) linear or branched alkyl group, or a heterocyclic or heterocyclo —($C_1$–$C_8$) linear or branched alkyl group, said heterocyclic group containing at least one heteroatom selected from the group consisting of nitrogen atom, optionally substituted with a ($C_1$–$C_8$) alkyl group, and/or oxygen and/or sulfur; said alkyl, alkenyl, cycloalkyl, cycloalkylalkyl, aryl, aryl-alkyl, heterocyclic or heterocyclo-alkyl groups, being optionally substituted with one or more groups selected from the group consisting of: halogen, hydroxy, keto, $C_1$–$C_8$ alkyl, $C_1$–$C_8$ alkoxy, phenyl, cyano, nitro, —$NR_6R_7$, wherein $R_6$ and $R_7$, the same or different between them, are hydrogen, ($C_1$–$C_8$) linear or branched alkyl; the —COOH group or a pharmaceutically acceptable ester thereof; or the -$CONR_8R_9$ group, wherein $R_8$ and $R_9$, the same or different between them, are hydrogen, ($C_1$–$C_8$) linear or branched alky, phenyl; or $R_4$ is a ($C_6$–$C_{10}$) aroyl or ($C_6$–$C_{10}$) arylsulfonyl group, optionally substituted with one or more groups selected from the group consisting of: halogen, hydroxy, $C_1$–$C_8$ linear or branched alky, $C_1$–$C_8$ linear or branched alkoxy, phenyl, cyano, nitro, —$NR_{10}R_{11}$, wherein $R_{10}$ and $R_{11}$, the same or different between them are hydrogen, $C_1$–$C_8$ linear or branched alkyl;

$R_4$ is a polyaminoalkyl group; or $R_4$ is a glycosyl group;

n is the number 0 or 1;

$R_5$ is hydrogen, $C_1$–$C_8$ linear or branched alkyl, $C_1$–$C_8$ linear or branched alkenyl, $C_3$–$C_{10}$ cycloalkyl, ($C_3$–$C_{10}$) cycloalkyl —($C_1$–$C_8$) linear or branched alkyl, $C_6$–$Cl_{14}$ aryl, ($C_6$–$C_{14}$) aryl —($C_1$–$C_8$) linear or branched alkyl;

$R_2$ and $R_3$, the same or different between them are hydrogen, hydroxy, $C_1$–$C_8$ linear or branched alkoxy;

their $N_1$-oxides, their single isomers, in particular the syn and anti isomers of the —$C(R_5)$=N—O(n)$R_4$ group, their possible enantiomers, diastereoisomers and relative mixtures, the pharmaceutically acceptable salts thereof and their active metabolites;

with the proviso that when $R_5$, $R_2$ and $R_3$ are hydrogen and n is 1, then $R_4$ is different from hydrogen.

The present invention comprises the use of the compounds of the above-mentioned formula (I) as active ingredients for medicaments, in particular for medicaments useful for the treatment of tumors. A further object of the present invention is also the use of the compounds of formula (I) as active ingredients for medicaments useful for treating viral infections. Another object of the present invention is also the use of the compounds of formula (I) as active ingredients for medicaments having antiplasmodium falciparum activity.

The present invention comprises pharmaceutical compositions containing compounds of formula (I) as active ingredients, in admixture with pharmaceutically acceptable vehicles and excipients.

The present invention comprises also processes for the preparation of compounds of formula (I), and the relative key intermediates.

DETAILED DESCRIPTION OF THE INVENTION

Within the scope of the present invention, as examples of $C_1$–$C_8$ linear or branched alkyl group, methyl, ethyl, propyl, butyl, pentyl, octyl are meant and their possible isomers, such as for example isopropyl, isobutyl, tert-butyl.

Examples of $C_1$–$C_8$ linear or branched alkenyl group are methylene, ethylidene, vinyl, allyl, propargyl, butylene, pentylene, wherein the carbon—carbon double bond, optionally in the presence of other carbon—carbon unsaturations, can be situated in the different possible positions of the alkyl chain, which can also be branched within the allowed isomery.

Examples of $C_3$–$C_{10}$ cycloalkyl group are cyclopropyl, cyclobutyl, cyclopentyl, cyclohexyl, cyclooctyl, polycyclic groups, such as for example adamantyl. Examples of ($C_3$–$C_{10}$) cycloalkyl - ($C_1$–$C_8$) linear or branched alkyl group are cyclopropylmethyl, 2-cyclopropylethyl, 1-cyclopropylethyl, 3-cyclopropylpropyl, 2-cyclopropylpropyl, 1-cyclopropylpropyl, cyclobutylmethyl, 2-cyclobutylethyl, 1-cycloburyelthyl, 3-cyclobutylpropyl, 2-cyclobutylpropyl, 1-cyclobutylpropyl, cyclohexylmethyl, 2-cyclohexylethyl, 1-cyclohexylethyl, 3-cyclohexylpropyl, 2-cyclohexylpropyl, 1-cyclohexylpropyl, 5-cyclohexylpentyl, 3-cyclohexylpentyl, 3-methyl-2-cyclohexylbutyl, 1-adamantylethyl, 2-adamantylethyl, adamantylmethyl.

Examples of ($C_6$–$C_{14}$) aryl, or ($C_6$–$C_{14}$) aryl - ($C_1$–$C_8$) linear or branched alkyl group are phenyl, 1- or 2-naphthyl, anthryl, benzyl, 2-phenylethyl 1-phenylethyl, 3-phenylpropyl, 2-anthrylpropyl, 1-anthrylpropyl, naphthylmethyl, 2-naphthylethyl, 1-naphthylethyl, 3-naphthylpropyl, 2-naphthylpropyl, 1-naphthylpropyl, cyclohexylmethyl, 5-phenylpentyl, 3-phenylpentyl, 2-phenyl-3-methylbutyl.

Examples of heterocyclic or heterocyclo - ($C_1$–$C_8$) linear or branched alkyl group are thienyl, quinolyl, pyridyl, N-methylpyperidinyl, 5-tetrazolyl, 2-(4,5-dihydroxazolyl), 1,2,4-oxadiazolidin-3-yl-5-one, purine and pyrimidine bases, for example uracyl, optionally substituted as shown in the general definitions above-mentioned.

Examples of ($C_6$–$C_{10}$) aroyl groups are benzoyl, naphthoyl.

Examples of ($C_6$–$C_{10}$) arylsulfonyl groups, optionally substituted with an alkyl group, are tosyl, benzenesulfonyl. As halogen it is intended fluorine, chlorine, bromine, iodine.

Examples of substituted groups are pentafluorophenyl, 4-phenylbenzyl, 2,4-difluorobenzyl, 4-aminobutyl, 4-hydroxybutyl, dimethylaminoethyl, p-nitrobenzoyl, p-cyanobenzoyl.

Examples of polyaminoalkyl group is —$(CH_2)m$—$NR_{12}$—$(CH_2)_p$—$NR_{13}$—$(CH_2)_q$—$NH_2$, wherein m, p are an integer from 2 to 6 and q is an integer from 0 to 6, extremes included and $R_{12}$ and $R_{13}$ are a ($C_1$–$C_8$) linear or branched alkyl group, for example N-(4-aminobutyl-)2-aminoethyl, N-(3-aminopropyl)-4-aminobutyl, N-[N-(3-aminopropyl)-N-(4-aminobutyl)]-3-aminopropyl.

Examples of glycosyl group are 6-D-galactosyl, 6-D-glucosyl, D-galactopyranosyl, the glycosyl group being optionally protected with a suitable ketal group, isopropylidene, for instance.

Examples of pharmaceutically acceptable salts are, in case of nitrogen atoms having basic character, the salts with pharmaceutically acceptable acids, both inorganic and organic, such as for example, hydrochloric acid, sulfuric acid, acetic acid, or, in the case of acid group, such as carboxyl, the salts with pharmaceutically acceptable bases, both inorganic and organic, such as for example, alkaline and alkaline-earth hydroxides, ammonium hydroxide, amine, also heterocyclic ones.

A first group of preferred compounds comprises the compounds of formula (I) wherein n is 1.

A second group of preferred compounds comprises the compounds of formula (I) wherein n is 0.

Within the two above mentioned preferred groups, the compounds of formula (I) are preferred, wherein $R_4$ is different from hydrogen, in particular is a $C_1$–$C_8$ linear or branched alkyl or $C_1$–$C_8$ linear or branched alkenyl group, or $C_3$–$C_{10}$ cycloalkyl, or ($C_3$–$C_{10}$) cycloalkyl —($C_1$–$C_8$) linear or branched alky, or $C_6$–$C_{14}$ aryl, or ($C_6$–$C_{14}$) aryl —($C_1$–$C_8$) linear or branched alkyl, or a heterocyclic or heterocyclo —($C_1$–$C_8$) linear or branched alkyl group, said heterocyclic group containing at least a heteroatom selected from the group consisting of nitrogen atom, optionally substituted with a ($C_1$–$C_8$) alkyl group, and/or oxygen and/or sulfur; said alkyl, alkenyl, cycloalkyl, aryl, aryl-alkyl, heterocyclic or heterocyclo-alkyl groups, being, optionally substituted with one or more groups selected from the group consisting of: halogen, hydroxy, $C_1$–$C_8$ alky, $C_1$–$C_8$ alkoxy, phenyl, cyano, nitro, —$NR_6R_7$, wherein $R_6$ and $R_7$, the same or different between them, are hydrogen, ($C_1$–$C_8$) linear or branched alkyl; the —COOH group or a pharmaceutically acceptable ester thereof; or the —$CONR_8R_9$ group, wherein $R_8$ and $R_9$, the same or different between them, are hydrogen, ($C_1$–$C_8$) linear or branched alkyl, according to the definitions given above by means of example.

A first group of particularly preferred compounds comprises:

7-methoxyiminomethylcamptothecin (CPT 179);
7- methoxyiminomethyl-10-hydroxycamptothecin (CPT 211);
7-(ter-butoxycarbonyl-2-propoxy)iminomethylcamptothecin (CPT 224);
7-ethoxyiminomethylcamptothecin;
7-isopropoxyiminomethylcamptothecin;
7-(2-methylbutoxy)iminomethylcamptothecin;
7-t-butoxyiminomethylcamptothecin (CPT 184);
7-t-butoxyiminomethyl-10-hydroxycamptothecin (CPT 212);
7-t-butoxyiminomethyl-10-methoxycamptothecin (CPT 220);
7-(4-hydroxybutoxy)iminomethylcamptothecin;
7-triphenylmethoxyiminomethylcamptothecin (CPT 192);
7-carboxymethoxyiminomethylcamptothecin (CPT 183);
7-(2-amino)ethoxyiminomethylcamptothecin (CPT 188);
7-(2-N,N-dimethylamino)ethoxyiminomethylcamptothecin (CPT 197);
7-allyloxyiminomethylcamptothecin (CPT 195);
7-cyclohexyloxyiminomethylcamptothecin;
7-cyclohexylmethoxyiminomethylcamptothecin;
7-cyclooctyloxyiminomethylcamptothecin;
7-cyclooctylmethoxyiminomethylcamptothecin;
7-benzyloxyiminomethylcamptothecin (CPT 172);
7-[(1-benzyloxyimino)-2-phenylethyl]camptothecin;
7-(1-benzyloxyimino)ethylcamptothecin (CPT 186);
7- phenoxyiminomethylcamptothecin (CPT 223);
7-(1-t-butoxyimino)ethylcamptothecin;
7-p-nitrobenzyloxyiminomethylcamptothecin (CPT 177);
7-p-methylbenzyloxyiminomethylcamptothecin (CPT 178);
7-pentafluorobenzyloxyiminomethylcamptothecin (CPT 182);
7-p-phenylbenzyloxyiminomethylcamptothecin (CPT 187);
7-[2-(2,4-difluorophenyl)ethoxy]iminomethylcamptothecin;
7-(4-t-butylbenzyloxy)iminomethylcamptothecin;
7-(1-adamantyloxy)imnomethylcamptothecin;
7-(1-adamantylmethoxy)iminomethylcamptothecin;
7-(2-naphthyloxy)iminomethylcamptothecin;
7-(9-anthrylmethoxy)iminomethylcamptothecin;
7-oxiranylmethoxyiminomethylcamptothecin (CPT 213);
7-(6-uracyl)methoxyiminomethylcamptothecin;
7-[2-(1-uracyl)ethoxy]iminomethylcamptothecin (CPT 199);
7-(4-pyridyl)methoxyiminomethylcamptothecin (CPT 189);
7-(2-thienyl)methoxyiminomethylcamptothecin;
7-[(N-methyl)-4-piperidinyl]methoxyiminomethylcamptothecin (CPT 190);
7-[2-(4-morpholininyl]ethoxy]iminomethylcamptothecin (CPT 210);
7-(benzoyloxyiminomethyl)camptothecin (CPT 191)
7-[(1-hydroxyimino)-2-phenylethyl)camptothecin (CPT 185);
7-ter-butyloxyiminomethylcamptothecin N-oxide (CPT 198);
7-methoxyiminomethylcamptothecin N-oxide (CPT 208);

A second group of particularly preferred compounds comprises:

7-[N-(4-aminobutyl)-2-aminoethoxy]iminomethylcamptothecin;
7-[N-[N-(3-amino-1-propyl)-4-amino-1-butyl]-3-aminopropoxy]iminomethylcamptothecin;
7-(6-D-galactosyloxy)iminomethylcamptothecin;
7-(1,2:3,4-di-O-isopropylydene-D-galactopyranosyloxy)iminomethylcamptothecin (CPT 215);
7-(6-D-glucosyloxy)iminomethylcarnptothecin (CPT 216);

A third group of particularly preferred comprises compounds:

7-t-butyliminomethylcamptothecin;
7-(4-amino)butyliminomethylcamptothecin;

7-(4-hydroxy)butyliminomethylcamptothecin (CP 169);
7-(2-N,N-dimethylamino)ethyliminomethylcamptothecin (CPT 171);
7-allyliminomethylcamptothecin;
7-cyclohexyliminomethylcamptothecin (CPT 156);
7-phenyliminomethylcamptothecin (CPT 154);
7-p-nitrophenyliminomethylcamptothecin (CPT 160);
7-benzyliminomethylcamptothecin (CPT 175);
7-(2-anthrylmethyl)iminomethylcamptothecin;
7-(2-quinolylmethyl)iminomethylcamptothecin;
7-(2-thienyl)iminomethylcamptothecin;
7-[N-[N-(3-amino-1-propyl)-4-amino-1-butyl]-3-aminopropyl]iminomethyl-camptothecin;
7-(6-D-galactosyl)iminomethylcamptothecin.

In a first preferred embodiment of the invention, compounds of general formula (I) are provided, wherein n is 1, therefore camptothecins 7-oxime, and $R_4$ is an alkyl or arylalyl group, as above defined.

Among these, the highly preferred compounds are:
7-(t-butoxy)iminomethylcamptothecin (CPT 184) of formula

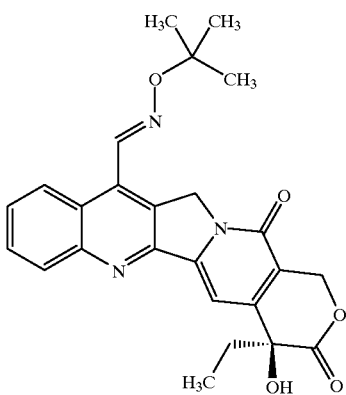

and
7-benzyloxyiminomethylcamptothecin (CPT 172).

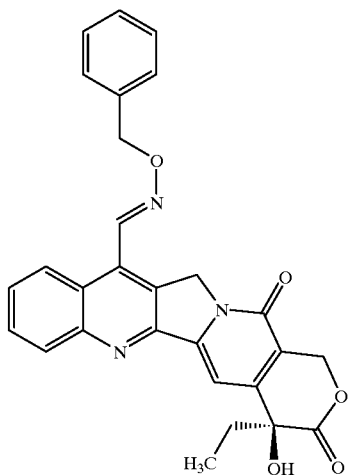

The compounds of formula (I) can be prepared with different methods according to the nature of the $R_4$ group and to the presence of the oxygen atom linked to the nitrogen of the 7-iminomethyl group.

Concerning the compounds of formula (I) wherein n is 1 and $R_4$ is as above defined, with the exception of aroyl and arylsulfonyl, can be prepared starting from camptothecin 7-aldehyde (formula Ia, $R_5$ hydrogen) or 7-keto camptothecin (formula Ia, $R_5$ different from hydrogen).

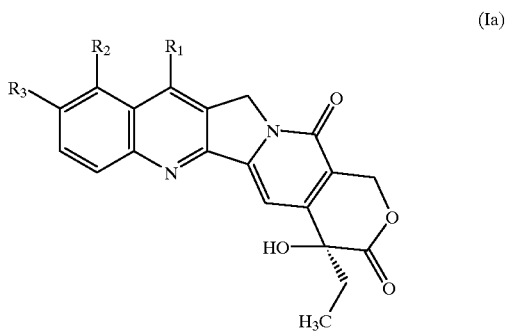

(Ia)

wherein $R_1$ is the group —$C(R_5)$=O, and $R_5$ is as defined for the formula (I), $R_2$ and $R_3$ are as defined in formula (I). The compound of formula (Ia) is reacted with the compound of formula (IIa) $R_4O$—$NH_2$, wherein $R_4$ is as above defined, to give compounds of formula (I), wherein $R_1$ is the group —$C(R_5)$=N—$OR_4$, $R_4$ is defined as in formula (I), except aroyl and arylsulfonyl. The reaction can be carried out with conventional methods well known to the person skilled in the art, being a normal formation of an oxime. Preferably, the molar ratio between 7-aldehyde or 7-keto camptothecin and hydroxylamine is comprised between 1:3 and 3:1. The salts of the hydroxyiamine of interest can also be used. The reaction is carried out in the presence of a base, for example an inorganic base, such as potassium carbonate, or organic, such as triethylamine or diazabicyclononene, using polar solvents, preferably methanol or ethanol and carrying out the reaction at a temperature comprised between room temperature and boiling point of the solvent used, optionally in the presence of dehydrating agents, for example sodium or magnesium sulfate, molecular sieves. If desired it is also possible to carry out the reaction in the presence of a catalyst, for example a Lewis acid.

Alternatively, the above compounds can be prepared from the oxime of the camptothecin 7-aldehyde (obtained as disclosed in Sawada et al Chem. Pharm. Bull. 39, (10) 2574 (1991)), or of a 7-keto by reacting with a halide $R_4$—X, wherein X is preferably iodine, in a polar solvent, for example tetrahydrofurane or alcohols, and in the presence of a base, for example sodium hydride or potassium carbonate.

As to the compounds of formula (I) wherein n is 1 and $R_4$ is aroyl or arylsulfonyl, as defined for the formula (I), these can be prepared starting from camptothecin 7-oxime, whose preparation is described in the previous paragraph, with acyl chlorides $R_4$—COCl, in polar solvents, and in the presence of a base, preferably pyridine, or directly in pyridine, as disclosed by Cho et al. J. Org. Chem. 62, 2230 (1997).

As far as the compounds of formula (I) wherein n is 0 and $R_4$ is as above defined, with the exception of aroyl, they can be prepared starting from camptothecin 7-aldehyde (formula Ia, $R_5$ hydrogen) or 7-keto camptothecin (formula Ia, $R_5$ different from hydrogen).

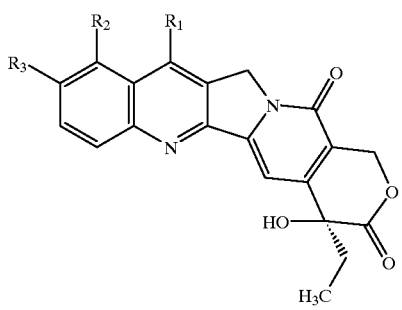

(Ia)

wherein $R_1$ is the group —$C(R_5)$=O, and $R_5$ is as defined for the formula (I), $R_2$ and $R_3$ are as defined in formula (I). The compound of formula (Ia) is reacted with the compound of formula (IIb) $R_4$—$NH_2$, wherein $R_4$ is as above, to give compounds of formula (I), wherein $R_1$ is the group —$C(R_5)$=N—$R_4$, $R_4$ is defined as in formula 1, except aroyl. The reaction can be carried out with conventional methods well known to the person skilled in the art, being a normal formation of an imine. Preferably, the molar ratio between 7-aldehyde or 7-keto camptothecin and amine is comprised between 1:3 and 3:1. The salts of the amine of interest can also be used. The reaction is carried out in the presence of a base, for example an inorganic base, such as potassium carbonate, or organic, such as triethylamine or diazabicyclononene, using polar solvents, preferably methanol or ethanol and carrying out the reaction at a temperature comprised between room temperature and solvent boiling point, optionally in the presence of dehydrating agents, for example sodium or magnesium sulfate, molecular sieves. If desired it is also possible to carry out the reaction in the presence of a catalyst, for example a Lewis acid (as disclosed for example by Moretti and Torre, *Synthesis*, 1970, 141; or by Kobayashi et al, Synlett, 1977, 115).

The camptothecin 7-aldehyde and the camptothecin 7-oxime are disclosed in the patent application EP 0056692 and in the mentioned Sawada et al Chem. Pharm. Bull. 39, (10) 2574 (1991), $N_1$-oxides of the compounds of formula (I) are prepared according to well-known methods of oxidation of heteroaromatic nitrogen, preferably by oxidation with acetic or trifluoroacetic acid and hydrogen peroxide, or by reaction with organic peroxyacids (A. Albini and S. Pietra, Heterocyclic N-oxides, CRC, 1991).

Regarding the various meanings of $R_4$, present in the different reactives of formula II, these reactives are available in the market, or can be prepared according to well-known methods in literature, which the expert in the field can resort to, completing with their own knowledge of the argument.

Pharmaceutically acceptable salts are obtained with conventional methods found in the literature, and do not necessitate of further disclosure.

The compounds disclosed in the present invention show antiproliferative activity, therefore are useful for their therapeutical activity, and posses physico-chemical properties that make them suitable to be formulated in pharmaceutical compositions.

The pharmaceutical compositions comprise at least a compound of formula (I), in an amount such as to produce a significant therapeutical effect, in particular antitumoral effect. The compositions comprised within the present invention are conventional and are obtained with commonly used methods in the pharmaceutical industry. According to the desired administration route, the compositions shall be in solid or liquid form, suitable to the oral, parenteral, intravenous route. The compositions according to the present invention comprise together with the active ingredients at least a pharmaceutically acceptable vehicle or excipient. Formulation co-adjuvants, for example solubilizing, dispersing, suspending, emulsionation agents can be particularly useful.

The compounds of formula (I) can also be used in combination with other active ingredients, for example other antitumor drugs, both in separate forms, and in a single dose form.

The compounds according to the present invention are useful as medicaments with antitumor activity, for example in lung tumors, such as the non-small cell lung tumour, tumors of the colon-rectum, prostate, gliomas.

Cytotoxic activity of the compounds of the present invention was assayed in cell systems of human tumour cells, using the antiproliferative activity test as a method of evaluation of the cytotoxic potential.

The cell line used is a lung non-small cell carcinoma that belongs to non-small cells hystotype named NCI H460.

The preferred compounds 7-(t-butoxyiminomethylcamptothecin (CPT 184) and 7-benzyloxyiminomethylcamptothecin (CPT 172) were assayed in comparison with Topotecan (TPT), the reference standard accepted by the persons expert in the field, and with 7-hydroxyiminomethylcamptothecin (CPT 181), disclosed by Sawada et al in Chem. Pharm. Bull. 39(10), 2574–2580, (1991), being the closest structural analogue to the compounds of formula (I) according to the present invention.

For the in vivo studies, the solubilization was carried out in 10% DMSO in bidistilled water, being impossible the solubilization in saline, and the administration for the oral route was carried out at a volume of 10 ml/kg.

Antitumoral activity

Atimic nu/nu Swiss mice (Charles River, Calco, Italia), ageing 10–12 weeks were used. The animals were maintained in laminar flow rooms, according to the guidelines of the United Kingdom Co-ordination Committee Cancer Research. Experimental protocols were approved by the Ethical Committee for animal experimentation of Istituto Nazionale per lo Studio e Cura dei Tumori.

Tumour fragments of about 2×2×2 mm coming from mice to which were inoculated s.c. $10^6$ cells NCI H460/topo, were implanted s.c. bilaterally in groups of 5 mice each.

The animals were treated with the compounds when the tumour began to be palpable, according to the following scheme:

CPT172 (8 mg/kg, po) q4dx4
CPT172 (16 mg/kg, po) q4dx4
CPT172 (24 mg/kg, po) q4dx4
CPT172 (2 mg/kg, po) qdx5x10w
CPT181 (15 mg/kg, po) q4dx4
CPT181 (25 mg/kg, po) q4dx$^4$
CPT184 (2 mg/kg, po) q4dx4
CPT184 (5 mg/kg, po) q10dx6
Topotecan (15 mg/kg, po) q4dx4
Topotecan (10 mg/kg, po) q4dx4

Twice a week, using a Vernier caliper, the width, minimum diameter (1), length and maximum diameter (L) of the tumors were measured, in mm. The tumour volume (mm$^3$) was calculated according to the formula $l^2 \times L/2$. Efficacy of the molecule was evaluated as TVI percent of the treated group versus the control group according to the formula TVI%=100−(T/C×100), wherein T is the mean value of the tumour volume of the treated group and C of control one. A compound is considered active when TVI%>50.

The following Table 1 reports the experimental results.

TABLE 1

Antitumoral activity of the camptothecin analogues in the treatment of the lung carcinoma NCI H460

| Compound | Dose (mg/kg, p.o.) | Treatment scheme | Efficacy (TVI %) | Toxicity Lethality | Body weight loss (%) |
|---|---|---|---|---|---|
| CPT172 | 8 | q4dx4 | 77 | | |
| | 16 | q4dx4 | 88 | | |
| | 24 | q4dx4 | 97 | 0/4 | 6 |
| | 2 | qdx5x10w | 90 | 0/3 | 0 |
| CPT181 | 15 | q4dx4 | 40 | 0/4 | 0 |
| | 25 | q4dx4 | 70 | 0/4 | 0 |
| CPT184 | 2 | q4dx4 | 100 | 0/5 | 0 |
| | 5 | q10dx6 | 99 | 0/4 | 9 |
| TPT | 15 | q4dx4 | 94 | 0/4 | 0 |
| | 15 | q4dx4 | 89 | 0/5 | 10 |
| | 10 | q4dx4 | 64 | 0/5 | 0 |

TVI % was evaluated 5–10 days after the last treatment

CPT172 demonstrated an antitumoral efficacy at different doses and at different treatment schemes; CPT184 revealed to be a very active compound at low doses and at different treatment schemes, accordingly, both compounds are two particularly promising molecules for clinical application.

Further advantages of these molecules can be identified in the wide interval of effective doses, indicating an increase of therapeutic index and a higher handling in the therapeutic use, in particular if a prolonged administration in the time is foreseen, above all in the injectable formulations, with the use of variable schemes and doses. For such uses, compound CPT 172 appears more favourable in relation to the reduced toxicity.

An important drawback of conventional camptothecins is the reversibility of the their bond in the ternary complex (drug-DNA-enzyme). This reversibility affects drug efficacy, as it does not allow the transformation of the single strand DNA cleavage into double strand DNA cleavage during DNA synthesis.

Table 2 below shows the persistence of DNA cleavage to a selected number of in-vitro cleavage sites. After 20 minutes of incubation of the drug in the reaction mixture containing labelled DNA and the purified enzyme, sodium chloride (0.6 M) was added with the scope of assisting the dissociation of the ternary complex. The result, shown in the table as percentage of DNA cleavage persistence at the sites, examined after about 10 minutes, is an indication of an almost complete reversibility of the cleavages in the case of camptothecin and Topotecan and a marked persistence in the case of CPT 172 and CPT 184.

TABLE 2

Persistence of DNA cleavage stimulated by camptothecins and mediated by topoisomerase i on selected sites

| DRUG (10 im) | PERSISTENCE (%) |
|---|---|
| Camptothecin | 16 |
| Topotecan | 16 |
| CPT 181 | 28 |
| CPT 184 | 72 |
| CPT 172 | 80 |

The advantage offered by the compounds according to the present invention is evident in overcoming the limit of reversibility of the ternary complex with respect to the state of the art. In preclinical investigations, CPT 184 showed cytotoxic activity in various tumor cell lines.

This broad spectrum of anticancer activity was confirmed in mice transplanted with human tumor xenografts, including NSCLC (H460, A549), prostate ca. (JCA-1), glioblastoma (GBM/7), gastric ca. (MKN28), osteosarcoma (U20S), ovarian ca. (A2780/Dx, A2780/DDP) and colon (HT29, CoBA) carcinomas as well as in murine lung cancer (M109) and leukaemia model (L1210).

The preclinical data suggest that CPT 184 may be an active anticancer agent against human's cancers and in particular against non-small cell lung cancer (NSCLC), glioblastoma and prostate carcinoma (Table 3).

TABLE 3

Antitumor activity of CPT 172, CPT 184 vs TPT on different tumor models

| | CPT 184 | | CPT 172 | | TPT |
|---|---|---|---|---|---|
| | 2 mg/kg | 3 mg/kg | 20 mg/kg | 25 mg/kg | 15 mg/kg |
| H460 | 99 (5/8*) | — | — | 97 | 98 |
| HT29 | 92 | — | — | 88 | 65 |
| CoBA | 84 | 87 | 84 | 93 | 85 |
| GBM/7 | 97 (3/10*) | 98 (2/8*) | 93 (3/11*) | 98 (9/12*) | 96 (1/10*) |
| U87 | 80 | 87 | — | — | 82 |
| A2780 | 100 (1/8*) | — | — | — | 96 |
| A2780/Dx | 92 (1/8*) | 100 (8/8*) | — | — | 92 (2/10*) |
| A2780/DDP | 77 | 90 | — | — | 92 |
| IGROV-1 | 93 | 96 | — | — | 89 |
| JCA-1 | 98 (5/8*) | — | 98 | — | 95 |
| DU145 | 95 | — | — | — | 77 |
| L1210 | >400*** | — | — | >400** | 39 |

Results are expressed for solid tumors as TVI % = tumor volume inhibition = 100 − (tumor weight of treated group/mean tumor weight of control group × 100) and for L1210 as ILS % = percent increase in life span [(MST of treated group/MST of control group) × 100]− 100.
*no evidence of tumor at the end of the treatment lasting for about 10 days from the last administration.
**>50% and
***>80% of cured mice alive 120 d from leukemia injection.
H460 = NSCLC
HT29 and CoBA = colon ca
IGROV-1, A2780, A2780/Dx and A2780/DDP = ovarian ca
GBM/7 and U87 = glioblastoma
JCA-1 and DU145 = prostate ca
L1210 = murine leukemia Results are expressed for solid tumors as TVI%=tumor volume inhibition=100-(tumor weight of treated group/mean tumor weight of control group×100) and for L1210 as ILS%=percent increase in life span [(MST of treated group/MST of control group)×100]-100.

* no evidence of tumor at the end of the treatment lasting for about 10 days from the last administration.
 >50% and *>80% of cured mice alive 120 d from leukemia injection.
 H460 =VSCLC
 HT29 and CoBA =colon ca
 IGROV-1, A2780, A2780/Dx and A2780/DDP=ovarian ca
 GBM/7 and U87=glioblastoma
 JCA-1 and DU145=prostate ca
 L1210=murine leukemia The high cytotoxic potency of the compounds of the present invention, herein represented in an exemplary way withone of the preferrred compounds, CPT 184, is also reflected by the potent antitumor activity. Using a panel of tumor xenografts characterized by a significant responsiveness to Topotecan (TPT) (i.e. TVI>80%), the spectrum of antitumor activity of CPT 184, and in a wide sense by the compounds of the present invention, against a significant number of human tumor models was substantially imperoved. In particular, an impressive antitumor efficacy was found in the treatment of many tumor models, where complete regressions were achieved in a large number of treated animals. Moreover, the compounds of the present invention, in particular the CPT 184, were able to induce 100% CR in the A2780/DX tumor chracterized by a MDR-phenotype. This observation is of high importance, indicating that the compounds of the present invention are not a substrate for P-glycoprotein.

Additional therapeutic advantages of the compounds of the present invention are related to a) an improvement of the therapeutic index, b) drug efficacy in a large range of doses, c) evidence of efficacy using quite different schedules, making the compounds of the present invention less dependent on the treatment schedule than that of Topotecan.

The following examples further illustrate the invention.

EXAMPLE 1

7-benzyloxyiminomethylcamptothecin (CPT 172)

500 mg (1.33 mmoles) of 7-formylcamptothecin were dissolved into 100 ml of ethanol. 15 ml of pyridine and 638 mg (4 mmoles) of O-benzylhydroxylamine hydrochloride were added and were left for 5 hours to reflux. The solvent was evaporated under vacuum and the residue so obtained was purified by means of flash chromatography on silica gel using a mixture of hexane/ethyl acetate 4/6 as eluant.

Yield 65% m.p.: 200°–205° C. dec.

The obtained product is constituted by an about 8:2 mixture of the two syn and anti isomers (isomer A: Rf 0.32; isomer B, Rf: 0.19 on silica gel Merck 60 F254, eluant hexane/ethyl acetate 3/7).

HPLC: the analyses were carried out on an instrument equipped with a quaternary pump (HP 1050) with Rheodyne injector (20 $\mu$l loop) and with a diode array detector (Hp 1050) controlled by a software HPLC-ChemStation. Spectra acquisition was made from 200 to 600 nm and the chromatograms were registered at 360 and 400 nm.

A C18 reverse phase column (Rainin C18; 25×0.4 cm, Varian) was used with an RP18 precolumn. The analysis was carried out with a linear elution gradient, starting from acetonitrile:water 30:70 to acetonitrile 100% in 20 min, with 1 ml/min flow. Retention times were: 12.51 min for isomer B and 14.48 for isomer A.

1H-NMR (300 MHz; DMSO-$d_6$):

δ:0.88 (t, H3-18A+H3-18B), 1.87 (m, H2-19A+H2-19B), 5.18 (s, H2-5B), 5.21 (s, H2-PhB), 5.30 (H2-PhA), 5.40 (s, H2-5A), 5.45 (s, H2-17A+H2-17 6.53 (s, OHA+OHB), 7.3–7.6 (m, ArA+ArB+H-14A+H-14B), 7.75 (m, H-11A+H-11B). 7.85–7.95 (m, H10A+H-10B), 7.98 (dd, H-12B). 8.18–8.27 (m, H-12A+H9-B), 8.45 (s, CH=NB), 8.59 (dd, H-9A), 9.38 (s, CH=N A).

Mass m/z 481 (M$^+$ 100) 374 (30)330(70)300(30)273(20) 243(20)91(34).

EXAMPLE 2

7-t-butoxyiminomethylcamptothecin (CPT 184)

400 mg (1.06 mmoles) of 7-formylcamptothecin were dissolved in 80 ml of ethanol. 12 ml of pyridine and 400 mg (3.18 mmoles) of O-t-butylhydroxylamine hydrochloride were added and left for 4 hours to reflux. The solvent was evaporated under vacuum and the residue so obtained was purified by means of flash chromatography on silica gel using a mixture of hexane/ethyl acetate 4/6 as eluant. 322 mg (0.72 mmoles) of a yellow solid were obtained.

Yield 68% m.p.: 250° C. dec.

The obtained product is constituted by an about 8:2 mixture of the two syn and anti isomers (isomer A: Rf 0.31; isomer B. Rf: 0.24 on silica gel Merck 60 $F_{254}$, eluant hexane/ethyl acetate 3/7).

HPLC: the analyses were carried out on an instrument equipped with a quaternary pump (HP 1050) with Rheodyne injector (20 $\mu$l loop) and with a diode array detector (Hp 1050) controlled by a software HPLC-ChemStation. Spectra acquisition was made from 200 to 600 nm and the chromatograms were registered at 360 and 400 nm.

A C18 reverse phase column (Rainin C18; 25×0.4 cm, Varian) was used with an RP18 precolumn. The analysis was carried out with a linear elution gradient, starting from acetonitrile:water 30:70 to acetonitrile 100% in 20 min, with 1 ml/min flow. Retention times were: 12.92 min for isomer B and 14.61 for isomer A.

1H-NMR (300 MHz; DMSO-$d_6$):

δ: 0.88 (t, H3-18A+H3-18B), 1.30 (s, t-but.B), 1.47 (s, t-but.A) 1.87 (m, H2-19A+H2-19B) 5.18 (s, H2-5 B), 5.37 (H2-5 A), 5.42 (s, H2-17A+H2-17B), 6.54 (s, OHA+OHB), 7.35 (s, H-14A). 7.36 (s, H-14B) 7.69–7.83 (m, H-11A+H-11B), 7.85–7.98 (m, H-1OA+H-1OB), 8.07 (dd, H-9B), 8.16–8.27 (m, H-9A+H-12B) 8.40 (s, CHB), 8.62 (dd, H-12A), 9.31 (s, CHA).

Mass m/z 448 (M$^+$ 28) 391 (40)374(100)362(40)330(34) 57(17).

According to the same procedure the following compounds were prepared:

7-t-butoxyiminomethyl-10-hydroxycamptothecin (CPT 212); m.p. 195 dec.

1H NMR (DMSO-$d_6$) δ=0.88 (t, J=7.35 Hz, $H_3$-18) 1.45 (s, $CH_3$) 1.80–1.90 (m, $H_2$-19) 5.12 (s, $H_2$-5 anti) 5.33 s, $H_2$-5 syn) 5.45 (m, $H_2$-17 syn; H2-17 anti) 6.50 (s, —OH) 7.25 (d, J=2.57 Hz, H-9 anti) 7.30 (s, H-14 syn; H-14 anti) 7.43–7.50 (m, H-11 syn; H-11 anti) 7.70 (d, J=2.57 Hz, H-9 syn) 8.15 (d, J=9.19 Hz; H-12 syn, H-12 anti) 8.25 (s, —CH=N anti) 9.00 (s, —CH=N syn).

Mass m/z: 463 (M$^+$16) 419 (15) 407 (25) 390 (43) 346 (100) 318 (10).

7-t-butoxyiminomethyl-10-methoxycamptothecin (CPT 220); m.p.: 250° C. dec.

1H NMR (DMSO-$d_6$) 0.88 (t, J=7.35 Hz, $H_3$-18) 1.47 (s, 3 —$CH_3$) 1.80–1.93 (m, $H_2$-19) 3.95 (s, —$OCH_3$ anti) 3.98 (s, —$OCH_3$ syn) 5.17 (s, $H_2$-5 anti) 5.30–5.45 (m, $H_2$-5 syn; $H_2$-17 syn; $H_2$-17 anti) 6.50 (s, —OH) 7.29 (s, H-14) 7.56 (dd, J=9.19 Hz; J=2.57 Hz; H-11) 7.90 (d, J=2.57 Hz; H-9) 8.12 (d, J=9.19 Hz; H-12) 8.39 (s, —CH=N anti) 9.33 (s, —CH=N syn).

Mass m/z: 477 (M56, M) 421 (74) 404 (100) 392 (66) 360 (18.5) 303 (6) 274 (7.5).

7-p-nitrobenzyloxyiminomethylcamptothecin (CPT 177);

7-p-methylbenzyloxyiminomethylcamptothecin (CPT 178) m.p. 203° C. dec.

7-methoxyiminomethylcamptothecin (CPT 179) m.p. 230° C. dec.

7-methoxyiminomethyl-10-hydroxycamptothecin (CPT 211); m.p.: 268° C. dec.

1H NMR (DMSO-d$_6$) δ=0.87 (t, J=7.35 Hz, H$_3$-18) 1.80–1.90 (m, H$_2$-19) 4.13 (s, —OCH$_3$) 5.32 (s, H$_2$-5) 5.41 (s, H$_2$-17) 6.50 (s, —OH) 7.26 (s, H-14) 7.47 (dd, J=9.19 Hz; J=2.56 Hz, H-11) 7.75 (d, J=2.56 Hz, H-9) 8.08 (d, J=9.19 Hz, H-12) 9.04 (s, —CH=N).

7-pentafluorobenzyloxyiminomethylcamptothecin (CPT 182) m.p. 200° C. dec.

7-carboxymethoxyiminomethylcamptothecin (CPT 183);

7-(carboxydimethylmethoxy)iminomethylcamptothecin; m.p.: 193° C. dec.

1H NMR (CDCl$_3$) δ=1.02 (t, J=7.35 Hz, H$_3$-18) 1.69 (s, —CH$_3$) 1.72 (s, —CH$_3$) 1.81–1.95 (m, H$_2$-19) 3.60 (s, —OH) 5.24 (d, J=16.55 Hz, H-17A) 5.32 (s, H$_2$-5) 5.65 (d, J=16.55 Hz, H-17B) 7.64 (s, H-14) 7.67 (ddd, J=6.99 Hz; J=8.47 Hz; J=1.47 Hz, H-11) 7.80 (ddd, J=6.99 Hz; J=8.47 Hz; J=1.47 Hz, H-10) 8.10–8.16 (m, H-9; H-12) 9.10 (s, —CH=N).

7-(ter-butoxycarbonyl-2-propoxy) iminomethylcamptothecin (CPT 224); m.p.: 180° C. dec.

$^1$H NMR (DMSO-d$_6$) ε=0.88 (t, J=7 Hz, H$_3$-18) 1.44 (s, 3 -CH$_3$) 1.60 (s, 2 —CH$_3$) 1.80–1.92 (m, H$_2$-19) 5.27 (s, H2-5) 5.43 (s, H$_2$-17) 6.53 (s, —OH) 7.35 (s, H-14) 7.76 (ddd, J=8.46 Hz;J=8.46 Hz; J=1.47 Hz, H-11) 7.92 (ddd, J=8.46 Hz; J=8.46 Hz; J=1.47 Hz, H-10) 8.23 (dd, J=8.46 Hz; J=1.47 Hz, H-12) 8.65 (dd, J=8.46 Hz; J=1.47 Hz, H-9) 9.20 (s, —CH=N).

Mass m/z: 534 (M+1 3) 477 (29) 374 (55) 273 (10) 57 (100) 41(57).

7-p-phenylbenzyloxyiminomethylcamptothecin (CPT 187) m.p. 200–202° C. dec.

7-oxiranylmethoxyiminomethylcamptothecin (CPT 213);
$^1$H NMR (CDCl$_3$) δ=0.87 (t, J=7 Hz, H$_3$-18) 0.80–2.00 (m, J=7 Hz, H$_2$-19) 2.80 (1H, m, —CH$_2$—O) 3.05 (1H, m, —CH$_2$—O) 3.40 (m, —CH—O) 3.75 (s, —OH) 4.30(1H, m, —CH$_2$—O—N) 4.73 (1H, m, —CH$_2$—O—N) 5.33 (d, J=16 Hz, H-17A) 5.45 (s, H$_2$-5) 5.75 (d, J=16 Hz, H-17B) 7.70 (s, H-14) 7.75 (m, H-11) 7.85 (m, H-10) 8.15–8.35 (m, H-9; H-12) 9.12 (s, —CH=N).

7-(2-amino)ethoxyiminomethylcamptothecin (CPT 188); m.p. 220° C. dec.

7-(4-pyridyl)methoxyiminomethylcamptothecin (CPT 189) m.p. 220° C. dec, mass m/z M$^+$482

7-[(N-methyl)-4-pyperidinyl] methoxyiminomethylcamptothecin (CPT 190) m.p. 185–190° C. dec, mass m/z M$^+$502

7-ethoxyiminomethylcamptothecin;
7-isopropyloxyiminomethylcamptothecin;
7-(2-methylbutoxy)iminomethylcamptothecin;
7-cyclohexloxyiminomethylcamptothecin;
7-cyclohexylmethoxyiminomethylcamptothecin;
7-cyclooctyloxyiminomethylcamptothecin;
7-cyclooctylmethoxyiminomethylcamptothecin;
7-(1-adamantyloxy)iminomethylcamptothecin;
7-(1-adamantylmethoxy)iminomethylcamptothecin;
7-phenoxyiminomethylcamptothecin (CPT 223);
$^1$H NMR (DMSO-d$_6$) δ=0.89 (t, J=7.35 Hz, H$_3$-18) 1.81–1.95 (m, H$_2$-19) 5.25 (s, H$_2$-5 anti) 5.42 (s, H$_2$-17anti) 5.45 (s, H$_2$-5 syn) 5.52 (s, H$_2$-17 syn) 6.56 (s, —OH) 7.15–7.55 (m, 5Ar; H-14) 7.83 (m, H-11) 7.96 (m, H-10) 8.28 (dd, J=8.09 Hz; J=1.10 Hz, H-12) 8.73 (dd, J=8.09 Hz; J=1.10 Hz, H-9) 8.92 (s, —CH=N anti) 9.84 (s, —CH=N syn).

Mass m/z: 467 (M$^+$ 33) 373 (100) 329 (62) 314 (72) 273 (62) 244 (52) 135 (38) 57 (25) 43 (39).

7-(2-naphthyloxy)iminomethylcamptothecin;
7-(9-anthrylmethoxy)iminomethylcamptothecin;
7-[2-(2,4-difluorophenyl)ethoxy] iminomethylcamptothecin;
7-(4-t-butylbenzyloxy)iminomethylcamptothecin;
7-triphenylmethoxyiminomethylcamptothecin (CPT 192) m.p. 140° C. dec;
7-(2-N,N-dimethylaminoethoxy) iminomethylcamptothecin (CPT 197);
7-[N-(4-aminobutyl)-2-aminoethoxyliminomethylcamptothecin;
7-[N-[N-(3-amino-1-propyl)-4-amino-1-butyl]-3-aminopropoxy]iminomethylcamptothecin;
7-[2-(1-uracyl)ethoxy]iminomethylcamptothecin (CPT 199); m.p.: 197–200° C. dec.
$^1$H NMR (DMSO-d$_6$) δ=0.88 (t, J=7.35 Hz, H$_3$-18) 1.80–1.95 (m, H$_2$-19) 3.90 (t, J=6 Hz, —CH$_2$N anti) 4.15 (t, J=6 Hz, -CH$_2$N syn) 4.35 (t, J=6 Hz, —CH$_2$O anti) 4.58 (t, J=6 Hz, —CH$_2$O syn) 5.00 (d, J=8 Hz, H-5 U anti) 5.35–5.50 (m, H$_2$-5 anti; H$_2$-5 syn; H$_2$-17 anti; H$_2$-17 syn) 5.55 (d, J=8 Hz, H-5 U syn) 6.55 (s, —OH) 7.15 ( d, J=8 Hz, H-6 U anti) 7.40 (s, H-14) 7.64 (d, J=8 Hz;, H-6 U syn) 7.70–7.82 (m, H-10 syn; H-10 anti) 7.85–8.00 (m, H-11 syn; H-11 anti; H-12 anti) 8.23 (m, H-12 syn; H-9 anti) 8.48 (s, —CH=N anti) 8.60 (dd, J=8.46 Hz; J=1.47 Hz, H-9 syn) 9.35 (s,—CH=N syn) 11.3 (br s, NH U).

7-[2-(4-morpholinyl]ethoxyliminomethylcamptothecin (CPT 210); m.p.: 158–160° C. dec.

1H NMR (CDCl$_3$) δ=1.06 (t, J=7.35 Hz, H$_3$-18) 1.84–2.00 (m, H$_2$-19) 2.62 (t, J=4.78 Hz, —CH$_2$—N morf.) 2.87 (t, J=5.52 Hz, —CH$_2$—N) 3.60 (s, —OH) 3.79 (t, J=4.78 Hz, —CH$_2$—O morf.) 4.59 (t, J=5.52 Hz, —CH$_2$—O) 5.33 (d, J=16.18 Hz, H-17A) 5.45 (s, H$_2$-5) 5.77 (d, J=16.18 Hz; H-17B) 7.69 (s, H-14) 7.73 (ddd, J=1.47 Hz; J=8.46 Hz; J=8.46 Hz, H-11) 7.87 (ddd, J=1.47 Hz; J=8.46 Hz; J=8.46 Hz, H-10) 8.19–8.31 (m, H-9; H-12) 9.12 (s, —CH=N).

Mass m/z: 504 (M$^-$ 4) 373 (23) 329 (26) 272 (18) 244 (20) 216 (13) 100 (100).

7-(6-uracyl)methoxyiminomethylcamptothecin;
7-(4-hydroxybutoxy)iminomethylcamptothecin;
7-(2-thienyl)methoxyiminomethylcamptothecin;
7-(4-thiazolyl)methoxyiminomethylcamptothecin;
7-(6-D-galactosyloxy)iminomethylcamptothecin;
7-(6-D-glucosyloxy)iminomethylcamptothecin;
7-(6-D-glucosyloxy)iminomethylcamptothecin (CPT 216); m.p.: 210° C. dec.

$^1$H NMR (DMSO-d$_6$) δ=0.85 (t, J=7.3 Hz, H$_3$-18) 1.75–1.95 (m, H$_2$-19) 3.50–5.00 (m, 10H galact.) 5.35 (s, H$_2$-5) 5.45 (s, H$_2$-17) 6.25 (d, —OH galact.) 6.55 (s, -OH) 6.65 (d, -OH galact.) 7.35 (s, H-14) 7.80 (m, H-10) 7.98 (m,; H-11) 8.25 (dd, J=8.47 Hz; J=1.46 Hz, H-12) 8.60 (dd, J=8.47 Hz; J=1.46 Hz, H-9) 9.35 (s, —CH=N).

7-(1,2:3,4-di-O-isopropylydene-D-galactopyranosyloxy) iminomethylcamptothecin (CPT 215);

$^1$H NMR (DMSO-d$_6$) δ=0.87 (t, J=7.30 Hz, H$_3$-18) 1.30–1.45 (m, 4 —CH$_3$) 3.90–4.70 (m, H2-6'; H-5'; H-4'; H-3'; H-2') 1.80–1.93 (m, H$_2$-19) 5.35 (s, H$_2$-5) 5.45 (s, H$_2$-17) 5.60 (d, J=5.52 Hz, H-1') 6.52 (d, —OH) 7.35 (s, H-14) 7.75 (m, H-10 syn; H-10 anti) 7.90 (rn, H-11 syn; H-11 anti) 8.05 (dd, J=8.47 Hz; J=1.47 Hz, H-12 anti) 8.20 (m, H-12 syn; H-9 anti) 8.50 (s, —CH=N anti) 8.65 (dd, J=8.47 Hz; J=1.47 Hz; H-9 syn) 9.40 (s, —CH=N syn).

Mass m/z: 634 (M+1 13) 576 (10) 486 (18) 347 (35) 329 (45) 314 (49) 302 (28) 246 (100) 242 (55) 187 (26).

7-(1-benzyloxyimino)ethylcamptothecin (CPT 186);
7-[1(-t-butoxyimino)ethyl]camptothecin.

EXAMPLE 3

7-benzoylcamptothecin (CPT 170)

Sulfuric acid conc. (0.17 ml) and benzaldehyde (304 mg, 2.87 mmoles) were dropped into a suspension of camptothecin (200 mg, 0.57 mmoles) in $CH_3COOH$ (0.8 ml) and water (0.8 ml). The reaction mixture was cooled down to 0° C. and 80% t-butyl peroxide (128 mg, 1.14 mmol) and a solution of $FeSO_4$ (317 mg, 1.14 mmol) in water (0.56 ml) were subsequently added.

After stirring overnight at room temperature, water was added, a precipitate was obtained, which was filtered under vacuum. The mother liquors were extracted with methylene chloride (3 times); the organic phases were dried over $Na_2SO_4$, filtered and evaporated under vacuum. The solid thus obtained was gathered with the precipitate, which was separated before. The product was purified by means of flash chromatography on silica gel using as eluant a mixture of methylene chloride/methanol 98/2.90 mg (0.2 mmoles) of product were obtained.

Yield 35%

$^1$H-NMR (300 MHz; DMSO-$d_6$): δ=0.9 (t, 3H H3-18), 1.85 (m, 2H,H2-19), 5 (s, 2H,H2-5 5.4(2H,H2-5), 5.4 (s, 2H H2-17), 6.6(s, —1H OH), 7.4 (s1H,H14), 7.55–7.85 (m, 5H,H1-10,H-11,3Ar), 7.95–8 (m, 3H—H12 2Ar), 8.3 (dd, 1H—H-9).

EXAMPLE 4

7-[α-(hydroxyimino)benzyl]camptothecin (CPT 185)

A solution of 7-benzoylcamptothecin (50 mg, 0.1 1 mmoles), hydroxylamine hydrochloride (24 mg, 0.33 mmoles), pyridine (1.4 ml) in 10 ml of ethanol was prepared and left 24 hours to reflux. The solvent was eliminated under vacuum. The product was purified by means of flash chromatography on silica gel using a mixture of methylene chloride/methanol 98/2 as eluant. 25 mg of a yellow solid were obtained.

Yield 48%

The obtained product is constituted of a mixture of the two syn and anti isomers (isomer A: Rf 0.35; isomer B, Rf: 0.31 on silica gel Merck 60 $F_{254}$, eluant methylene chloride/methanol 95/5).

$^1$H-NMR (300 MHz; DMSO-$d_6$): δ: 0.9(t, H3-18A+H3-18B), 1.86 (m, H2-19A+H2-19B) 4.8 (m, H2-5 A+H2-5 B), 5.85 (s, H2-17A+H2-17B), 6.55 (s, —OH B), 7.60 (s OH A), 7.35–7.55 (m, Ar A+Ar B+H-10A+H-10B+H-11A+H-11B+H-14A+H-14B) 7.6–7.7 (m, H-12A+H-12B)

EXAMPLE 5

7-phenyliminomethylcamptothecin (CPT 154)

100 mg (0.26 mmoles) of 7-formylcamptothecin, dissolved into 20 ml of methylene chloride, and 25 μl (0.26 mmoles) of aniline, dissolved into 0.5 ml of methylene chloride, were added to a suspension of ytterbium triphlate (16.5 mg. 0.026 mmoles, 10 % mol) in 5 ml of methylene chloride containing MS 4A and were left 3.5 hours under stirring at room T, then the solvent was evaporated under vacuum. The product was purified by means of flash chromatography on silica gel using a mixture of methylene chloride/methanol 98/2 as eluant. 60 mg of a yellow solid were obtained.

Yield 51% m.p.: 255–258° C. dec

1H-NMR (300 MHz; DMSO-$d_6$): δ: 0.8 (t, 3H H3-18), 1.75 (m, 2H,H2-19), 5.35 (s, 2H,H2-5 ), 5.5 (s, 2H H2-17), 6.45 (s, -1H OH ), 7.25–7.35 (m, 2H H1-Ar+H-14), 7.4–7.5 (m,4H Ar), 7.75 (1H,ddd, H-11) 7.85 (ddd, 1H—H10), 8.2 (dd, 1H—H-12) 8.9 (dd, 1H, H-9), 9.6 (s, 1H, CH═N).

Following the same procedure the following compounds were prepared:

7-cyclohexyliminomethylcamptothecin (CPT 156);

7-p-nitrophenyliminomethylcamptothecin (CPT 160), m.p. 260–265° C. dec;

7-(4-hydroxy)butyliminomethylcamptothecin (CP 169) m.p. 140° C. dec;

7-dimethylaminoethyliminomethylcamptothecin (CPT 171);

7-benzyliminomethylcamptothecin (CPT 175);

7-t-butyliminomethylcamptothecin;

7-allyliminomethylcamptothecin;

7-(2-thienyl)iminomethylcamptothecin;

7-(4-amino) butyliminomethylcamptothecin;

7-(3-aminopropyl-4-aminobutyl-3-aminopropyl) iminomethylcamptothecin;

7-(2-anthrylmethyl)iminomethylcamptothecin;

7-(6-D-galactosyl)iminomethylcamptothecin;

7-(2-quinolylmethyl)iminomethylcamptothecin.

EXAMPLE 6

7-(benzoyloxyiminomethylmethyl)camptothecin (CPT191)

A solution of benzoyl chloride (0.16 ml, 1.4 mmoles) in 5 ml of pyridine was prepared and 500 mg (1.3 mmoles) of 7-hydroxyiminomethylcamptothecin were added and left overnight under stirring at room temperature. After evaporating pyridine under vacuum, a solution of sodium bicarbonate was added and it was extracted three times with methylene chloride. After drying with sodium sulfate and filtration, the solvent was evaporated off. The product was purified by means of flash chromatography on silica gel using a mixture of methylene chloride/methanol 98/2 as eluant. 200 mg (0.04 mmoles) of a yellow solid were obtained.

Yield 32%.

m.p.: 210C dec $^1$H-NMR (300 MHz; DMSO-$d_6$): δ: 0.8(t. H3-), 1.8 (m, H2) 5.45 (s, H2-5), 5.55 (s, H2-17), 6.6 (s, 1H —OH), 7.3 (s 1H, H-14), 7.75–8 (m, 5H H-10+H-11+3Ar) 8.25 (m, 2H, 2Ar) 8.3 (dd, 1H, H-12) 8.75 (dd, 1H, H-9), 10.05 (s, 1H, CH═N).

Following the same procedure the following compounds were prepared:

7-p-nitrobenzoyloxyiminomethylcamptothecin 7-p-cyanobenzoyloxyiminomethylcamptothecin 7-p-tolylsulfonyloxyiminomethylcamptothecin

EXAMPLE 7

7-t-butoxyiminomethylcamptothecin N-oxide (CPT 198)

7-t-butoxyiminomethylcamptothecin (30 mg, 0.067 mmol) was dissolved in acetic acid (5.2 ml) and 30% hydrogen peroxide was added. The mixture was heated at 70–80° C. for 9 hours, condensed to about one third and the residue was poured into ice-water. The precipitate material was collected by suction and purified by flash chromatography using a mixture of hexane/ethyl acetate 1/1 as eluent to afford 7-t-butoxyiminomethylcamptothecin N-oxide as a yellow power. (15.5 mg). Yield 50% m.p.: 185–190° C. dec.

$^1$H NMR (DMSO-d$_6$) δ=0.87 (t, J=7 Hz, H$_3$-18) 1.48 (s, 3 —CH$_3$) 1.76–1.95 (m, H2-19) 5.37 (s, H2-5) 5.42 (s, H$_2$-17) 6.60 (s, —OH) 7.85–8.00 (m, H-10; H-11) 8.15 (s, H-14) 8.65–8.75 (m, H-9; H-12) 9.2 (s, —CH=N).

According to the same procedure the following compounds were prepared:

7-methoxyiminomethylcamptothecin N-oxide (CPT 208)
1H NMR (DMSO-d$_6$) δ=0.87 (t, J=7.35 Hz, H$_3$-18) 1.78–1.93 (m, H$_2$-19) 4.12 (s, —OCH$_3$) 5.35 (s, H$_2$-5) 5.43 (s, H$_2$-17) 6.54 (s, —OH) 7.84–8.00 (m, H-10; H-11) 8.11 (s, H-14) 8.68–8.73 (m, H-9; H-12) 9.21 (s, —CH=N).

7-(carboxydimethylmethoxy)iminomethylcamptothecin N-oxide 7-(hydroxymethyldimethylmethoxy)iminomethylcamptothecin N-oxide.

EXAMPLE 8

7-p-nitrobenzyloxyiminomethylcamptothecin (CPT 177)

To a suspension of 7-hydroxyiminomethylcamptothecin (40 mg, 0.102 mmol) and sodium carbonate (10.9 mg, 0.102 mmol) in ethanol (4 ml), 4-nitrobenzylbromide (22 mg, 0.102 mmol) was added and the mixture was refluxed for 2.5 hours. The solvent was evaporated under reduced pressure and the residue was purified by flash chromatography using a mixture of hexane/ ethyl acetate 3/7 as eluent to afford 10.5 mg of 7-p-nitrobenzyloxyiminomethylcamptothecin.

Yield 20%

$^1$H NMR (DMSO-d$_6$) δ=0.88 (t, J=7 Hz, H$_3$-18) 1.80–1.92 (m, H$_2$-19) 5.23 (s, CH$_2$—O) 5.45(s, H$_2$-5) 5.57 (s, H$_2$-17) 6.55 (s, —OH) 7.35 (s, H-14) 7.75–7.95 (m, 2Ar; H-10; H-11) 8.2–8.4 (m, 2Ar; H-12) 8.65 (dd, J=8.46 Hz; J=1.47 Hz, H-9) 9.50 (s, —CH=N).

According to the same procedure the following compounds were prepared:

7-p-methylbenzyloxyiminomethylcamptothecin (CPT 178) m.p 203° C. dec.

7-pentafluorobenzyloxyiminomethylcamptothecin (CPT 182) m.p. 200° C. dec.

What is claimed is:

1. A compound selected from the group consisting of:

7-t-butyliminomethylcamptothecin;

7-(4-amino)butyliminomethylcamptothecin;

7-(4-hydroxy)butyliminomethylcamptothecin;

7-(2-N,N-dimethylamino)ethyliminomethylcamptothecin;

7-allyliminomethylcamptothecin;

7-cyclohexyliminomethylcamptothecin;

7-phenyliminomethylcamptothecin;

7-p-nitrophenyliminomethylcamptothecin;

7-benzyliminomethylcamptothecin;

7-(2-anthrylmethyl)iminomethylcamptothecin;

7-(2-quinolylmethyl)iminomethylcamptothecin;

7-(2-thienyl)iminomethylcamptothecin;

7-[N-[N-(3-amino-1-propyl)-4-amino-1-butyl]-3-aminoprop yl)iminomethylcamptothecin; and 7-(6-D-galactosyl)iminomethylcamptothecin.

2. A pharmaceutical composition comprising a therapeutically effective amount of a compound of claim 1, in admixture with pharmaceutically acceptable vehicle and excipient.

3. A pharmaceutical composition of claim 2 also including another active ingredient.

4. A pharmaceutical composition according to claim 3, wherein the other active ingredient is an antitumoral.

* * * * *